(12) United States Patent
Nielsen et al.

(10) Patent No.: US 6,840,922 B2
(45) Date of Patent: *Jan. 11, 2005

(54) MEDICAL PUNCTURING DEVICE

(75) Inventors: Jan Willum Nielsen, Roskilde (DK); Bjørn Gullak Larsen, Roskilde (DK); Orla Mathiasen, Roskilde (DK); Marc Delzac, Roskilde (DK); Claude Teisen-Simony, Frederiksberg (DK)

(73) Assignee: Unomedical A/S (DK)

( * ) Notice: Subject to any disclaimer, the term of this patent is extended or adjusted under 35 U.S.C. 154(b) by 247 days.

This patent is subject to a terminal disclaimer.

(21) Appl. No.: 10/017,789

(22) Filed: Dec. 13, 2001

(65) Prior Publication Data

US 2002/0045867 A1 Apr. 18, 2002

Related U.S. Application Data

(63) Continuation of application No. 09/115,340, filed on Jul. 14, 1998, now Pat. No. 6,355,021.

(51) Int. Cl.⁷ ................................................ A61M 5/00
(52) U.S. Cl. ........................ 604/263; 604/272; 604/198; 128/919
(58) Field of Search ............................. 604/93.01, 110, 604/181, 187, 192, 198, 263, 264, 268, 272, 288, 289, 523; 128/917, 919

(56) References Cited

U.S. PATENT DOCUMENTS

| | | |
|---|---|---|
| 4,838,871 A | 6/1989 | Luther |
| 4,982,842 A | 1/1991 | Hollister |
| 5,011,475 A | 4/1991 | Olson |
| 5,116,325 A | 5/1992 | Paterson |
| 5,147,319 A | 9/1992 | Ishikawa et al. |
| 5,176,662 A | 1/1993 | Bartholomew et al. |
| 5,188,611 A | 2/1993 | Orgain |
| 5,279,591 A | 1/1994 | Simon |
| 5,490,841 A | 2/1996 | Landis |
| 5,522,803 A | 6/1996 | Teissen-Simony |
| 5,533,974 A | 7/1996 | Gaba |
| 5,545,143 A | 8/1996 | Fischell |
| 5,599,318 A | 2/1997 | Sweeney et al. |
| 5,662,617 A | 9/1997 | Odell et al. |
| 5,665,075 A | 9/1997 | Gyure et al. |
| 5,704,920 A | 1/1998 | Gyure |
| 5,925,032 A | 7/1999 | Clements |
| 5,951,523 A | 9/1999 | Osterlind et al. |
| 5,957,892 A | 9/1999 | Thorne |
| 5,980,488 A | 11/1999 | Thorne |
| 5,984,897 A | 11/1999 | Petersen et al. |
| 6,355,021 B1 * | 3/2002 | Nielsen et al. ............ 604/263 |

FOREIGN PATENT DOCUMENTS

| | | |
|---|---|---|
| EP | WO 93/05840 | 4/1993 |
| EP | 744 183 A2 | 11/1996 |
| FR | 2 725 902 | 10/1994 |

* cited by examiner

*Primary Examiner*—Patricia Bianco
(74) *Attorney, Agent, or Firm*—Brinks Hofer Gilson & Lione

(57) ABSTRACT

The invention relates to a medical puncturing device comprising a rigid needle being at one end adapted for facilitating the puncturing and comprising at the opposite end a hub, the hub comprising a handle part and a shield part being pivotable in relation to the handle part and further comprising locking means on the shield part and the handle part, the locking means being adapter to interlock the shield and the handle part in a pivoted position of the shield part where the rigid needle is covered by this.

23 Claims, 6 Drawing Sheets

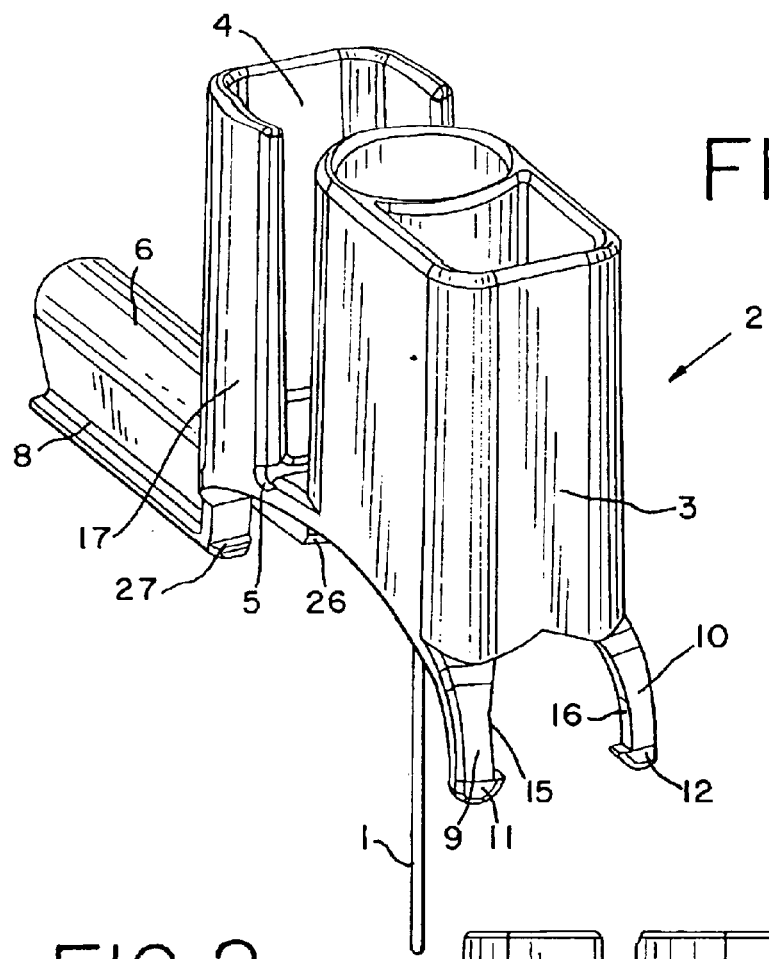
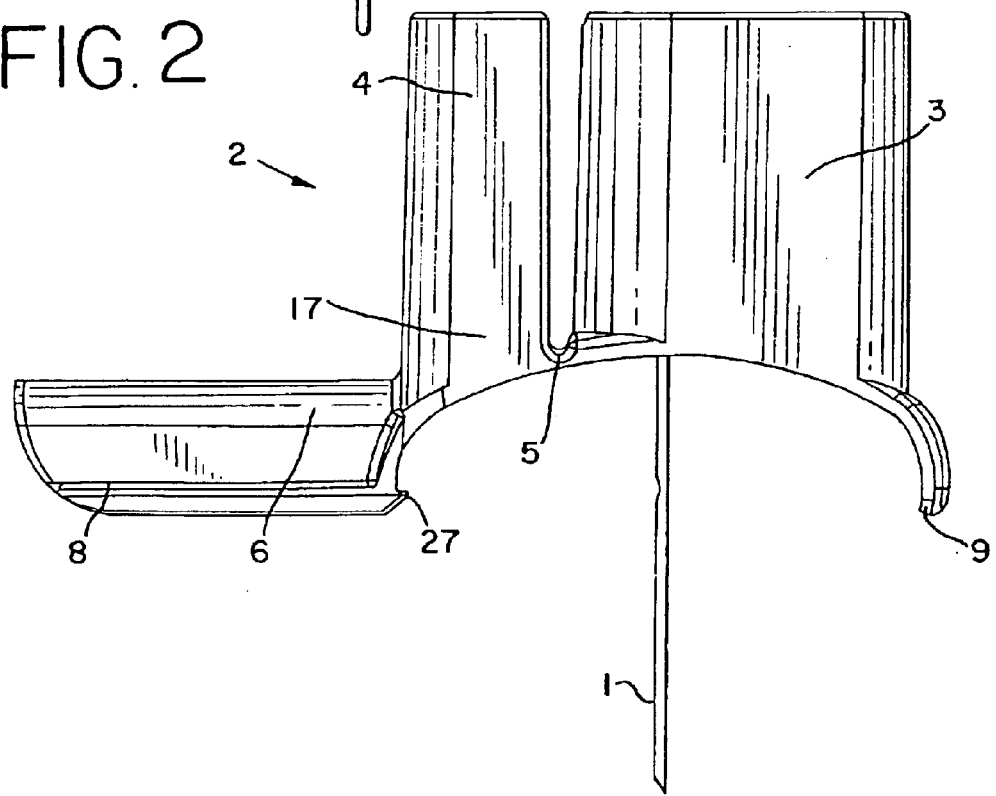

FIG. 3
FIG. 4
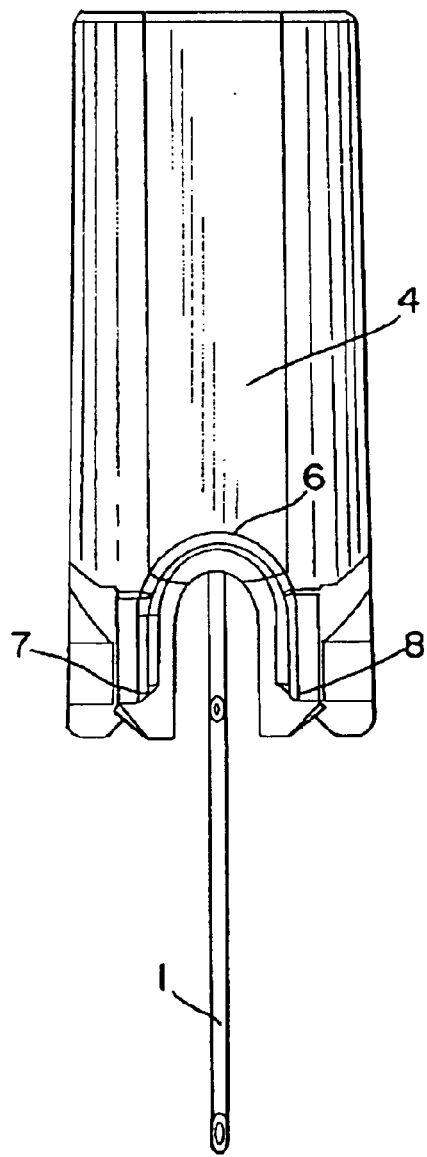
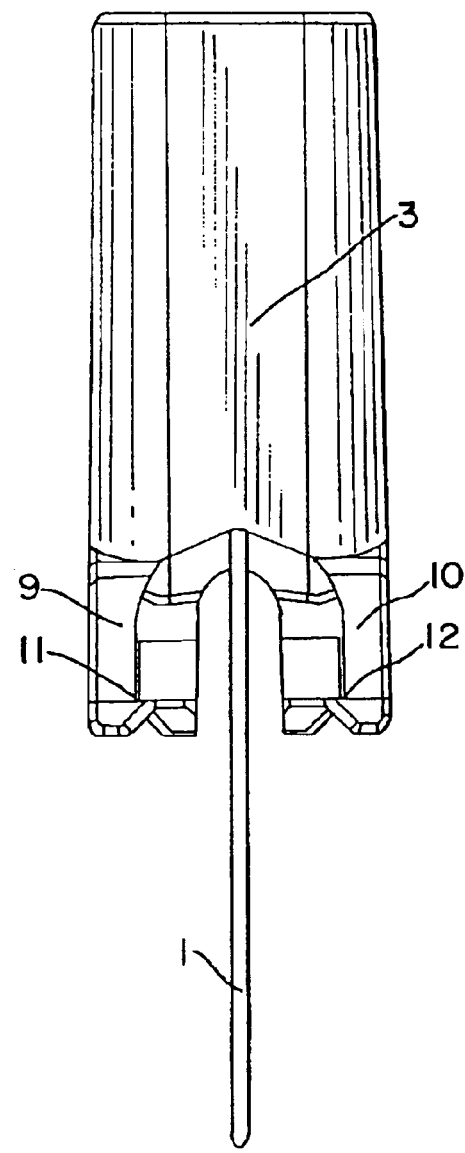

FIG. 5
FIG. 6
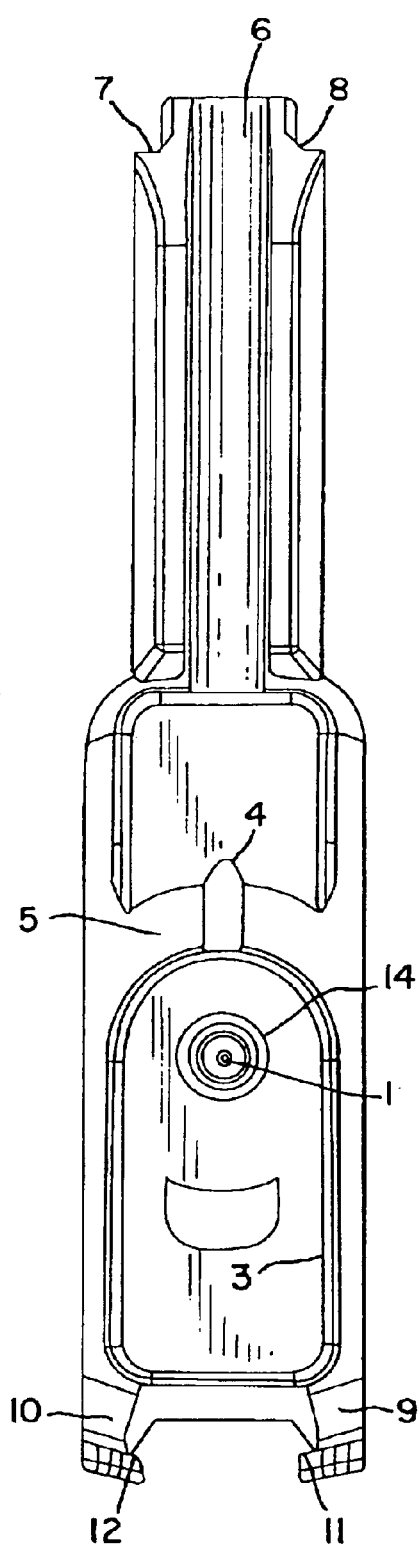
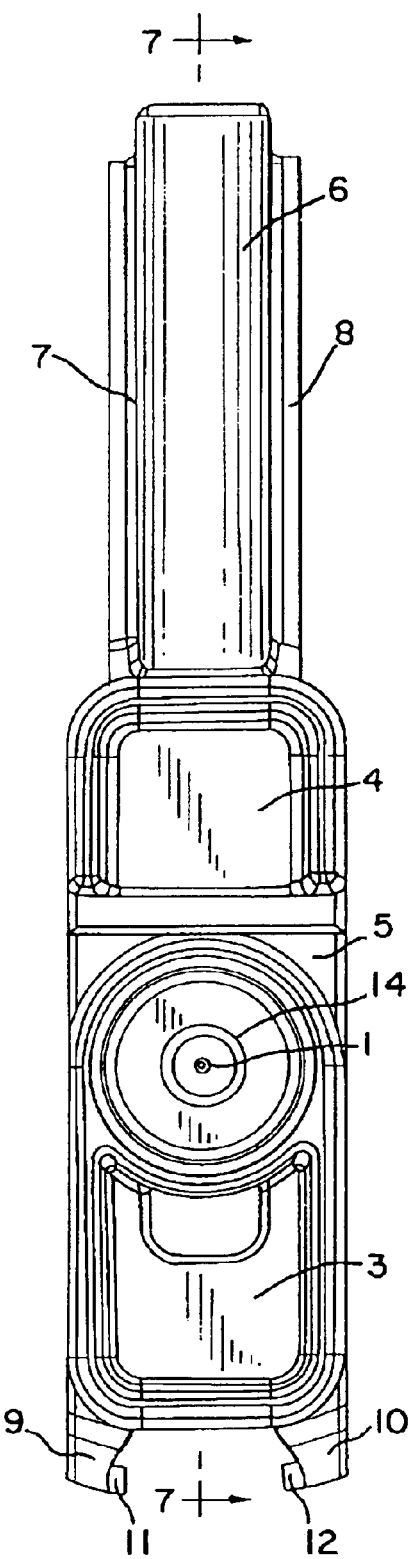

MEDICAL PUNCTURING DEVICE

This is a continuing patent application of application Ser. No. 09/115,340 filed Jul. 14, 1998, now U.S. Pat. No. 6,355,021 B1.

BACKGROUND OF THE INVENTION

The present invention relates to a medical puncturing device e.g. for use in connection with the insertion of a soft cannula where the soft cannula e.g. forms part of a infusion device for subcutaneous delivery of a medication or a therapeutic fluid by means of an external infusion system and more particularly to a medical puncturing device capable of being discarded without the danger of causing unintended harmful injuries to persons afterwards.

The medical puncturing device will in the following be explained in connection with the field of subcutaneous infusion devices. Such infusion devices are generally known in the art for delivering a medication or a therapeutic fluid to a subcutaneous site in a patient. Such devices commonly comprise a soft tubular cannula extending from a housing adapted to receive the desired medication via means, e.g. disconnectable means, for suitable connection to further components of the infusion system. The possibility of disconnecting the infusion set from the further parts of the infusion system is provided in order to improve the user comfort. In order to place the soft cannula at a subcutaneous delivery site, a medical puncturing device comprising a rigid needle and a handle is used. The rigid needle is inserted through the hollow soft cannula and extends beyond the outer tip of this. The soft cannula is inserted into the subcutaneous fat layer of the patient together with the rigid needle, which is afterwards withdrawn leaving the soft cannula at the infusion site. In order to provide such disconnectable medical puncturing device and still maintain a fluid-tight sealing towards the interior of the housing and the tubular cannula that prevents contamination of the infusion site, such devices are commonly provided with a self-sealing penetrable septum on the housing. Upon withdrawal of the needle from the septum this provides a fluid-tight sealing towards the interior of the housing. The septum and the needle further provides a fluid-tight sealing between the housing and the connector means when medication or therapeutic fluid is delivered to the patient from the external infusion system. Subcutaneous infusion devices of this generally known type are known from e.g. U.S. Pat. No. 5,522,803 to Teissen-Simony and U.S. Pat. No. 5,545,143 to Fischell.

The use of a medical puncturing device comprising a rigid needle may lead to some disadvantages during use of such device, viz, the potential danger of unintended exposure to the needle tip after the needle has been discarded.

A medical puncturing device of a type providing some remedy for these disadvantages is disclosed in U.S. Pat. No. 5,533,974. This previously known device comprises a rigid needle and a protector housing wherein a biasing element, a cam and a gripping element are provided in order to lock the protector housing in relation to the needle at the pointed tip of this.

A further device is disclosed in U.S. Pat. No. 5,279,591. This previously known device comprises a rigid needle and a protector housing wherein a resilient spring means is provided to block the needle tip upon sliding the protector housing to the needle tip.

A still further device is disclosed in WO 9305840. This previously known device comprises a rigid needle and a protector housing wherein a resilient guard element is provided to block the pointed needle tip upon sliding the protector housing to the needle tip. Means for limiting the sliding movement are provided hereby ensuring the position of the protector housing.

Although these previously known medical puncturing devices to some extent give a satisfactory result with respect to the prevention of unintended and harmful needle sticks they all have a complicated construction requiring a cumbersome assembling process.

For this reason there is a need for improvements in the field of medical puncturing devices, the improvements relating to providing a medical puncturing device having satisfactory properties particularly with respect to providing a medical puncturing device which can be dismantled and discarded without the risk of causing any injuries, and at the same time being of a simpler construction requiring less effort in the manufacturing process.

The infusion needle according to the invention remedies the above mentioned disadvantages and provides further advantages which will become apparent from the following description.

SUMMARY OF THE INVENTION

In order to provide remedy for the above mentioned disadvantages a medical puncturing device has been developed, said medical puncturing device comprising a rigid needle being at one end adapted for facilitating the puncturing and comprising at the opposite end a hub, the hub comprising a handle part and a shield part being pivotable in relation to the handle part and further comprising locking means on the shield part and the handle part, the locking means being adapted to interlock the shield and the handle part in a pivoted position of the shield part where the rigid needle is covered by this.

By these features a simple construction is obtained which provides a reliable function as to preventing the risk of causing any injuries upon dismantling and discarding of the device.

In a preferred embodiment the shield part comprises a recess for accommodating the rigid needle. This can conveniently be obtained by configuring the shield part with an essentially U-shaped cross section.

The locking means on the handle part preferably comprises two arms having on their opposed sides barbs adapted to interlocks with the corresponding locking means of the shield part. The locking means on the shield part preferably comprises two side flanges adapted to interlock with the corresponding locking means of the handle part. The flanges or the barbs are preferably tapered to facilitate the insertion of these into the corresponding locking means of the handle part and the shield part, respectively.

In order to facilitate the handling, the shield part preferably comprises an operating handle.

The hub is conveniently configured as a single part where the transition area between the handle part and the shield part is an area with a reduced rigidity, e.g. an area with a reduced material thickness. The medical puncturing device according to the invention is preferably manufactured from a plastics material, e.g. by a moulding process.

In a convenient embodiment the hub is prior to pivoting of the shield part adapted to grip around a body, e.g. an infusion device where a soft cannula belonging to this is to be inserted into a human body.

BRIEF DESCRIPTION OF THE DRAWINGS

FIG. 1 is a perspective view of a medical puncturing device;

FIG. 2 is a side view of the medical puncturing device shown in FIG. 1;

FIG. 3 is a rear end view of the medical puncturing device shown in FIG. 2;

FIG. 4 is a front end view of the medical puncturing device shown in FIG. 2;

FIG. 5 is a bottom view of the medical puncturing device shown in FIG. 1;

FIG. 6 is a top view of the medical puncturing device shown in FIG. 1;

DESCRIPTION OF THE PREFERRED EMBODIMENT

Figure 7:
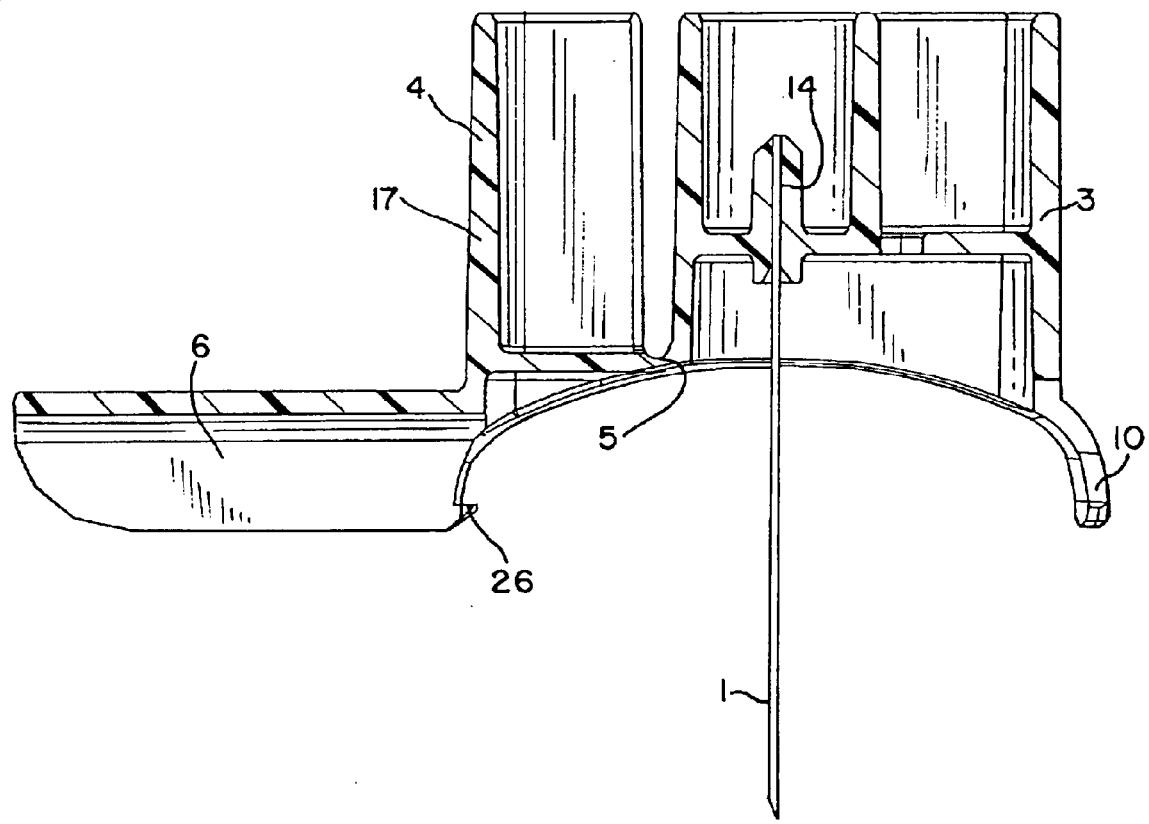
FIG. 7 is a sectional view after the line 7—7 in FIG. 5.

From FIG. 1 a preferred embodiment of the medical puncturing device appears. The device comprises a rigid needle 1 mounted in a needle hub 2. The needle is at the end opposite the needle hub 2 pointed or tapered so as to facilitate puncturing e.g. by the insertion of a soft cannula. The needle hub comprises a handle part 3, which is at one side connected to a shield part 4 via a hinge 5 formed as a material area with a reduced thickness. The shield part 4 has the shape of a half tube 6 having at the edges at both sides flanges 7, 8. The shield part 4 comprises a pivoting handle 17. At the opposite side of the needle hub 2 in relation to the needle connection point the needle hub 2 comprises two arms 9, 10 having barbs 11,12 at their opposed sides 15,16.

From FIG. 2 the puncturing device appears in a side view more clearly showing the transition area 5 where the shield part 4 is pivoted in relation to the handle part 3 by a pivoting action on the pivoting handle 17 by one hand while holding the handle part 3 with the other hand.

From FIG. 3 and FIG. 4 which are rear and front end views, respectively, the locking elements on the shield part and the handle part appear more clearly. Upon pivoting of the shield part in relation to the handle part these locking elements are caused to interact.

FIG. 5 and FIG. 6, which are bottom and top views, respectively, illustrate the locking elements in further detail.

From FIG. 7 the fastening site 14 for the rigid needle in the hub becomes apparent. The rigid needle is preferably secured in the correct position by a press fit connection or by gluing or welding.

Figure 8:
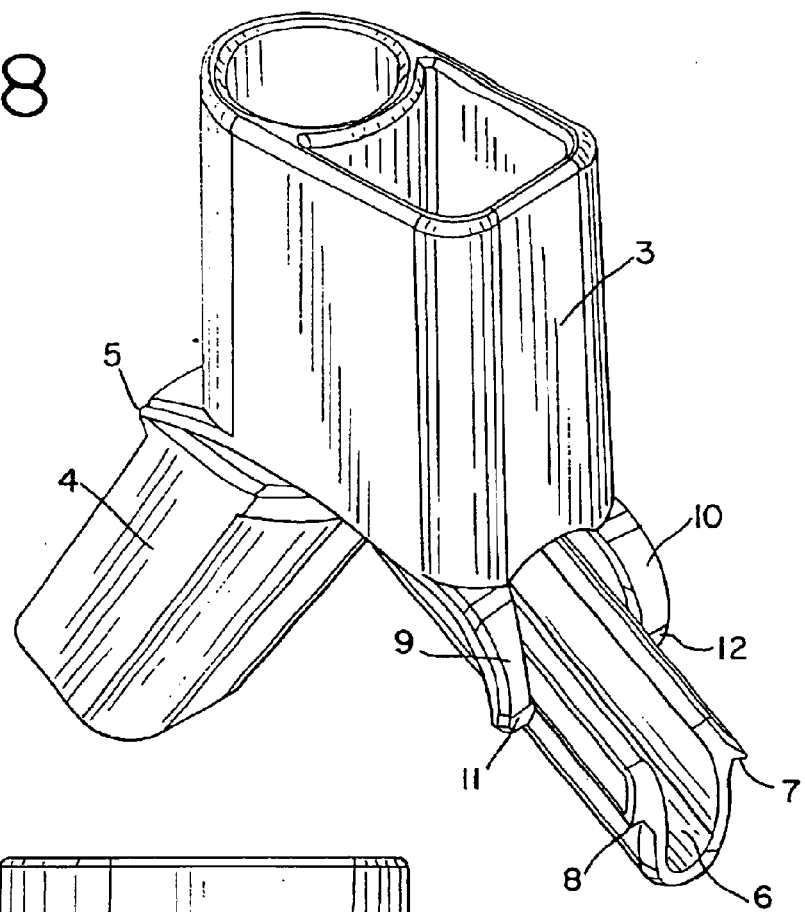
FIG. 8 is a perspective view showing the medical puncturing device where the shield part is pivoted to a locked position.
Figure 9:
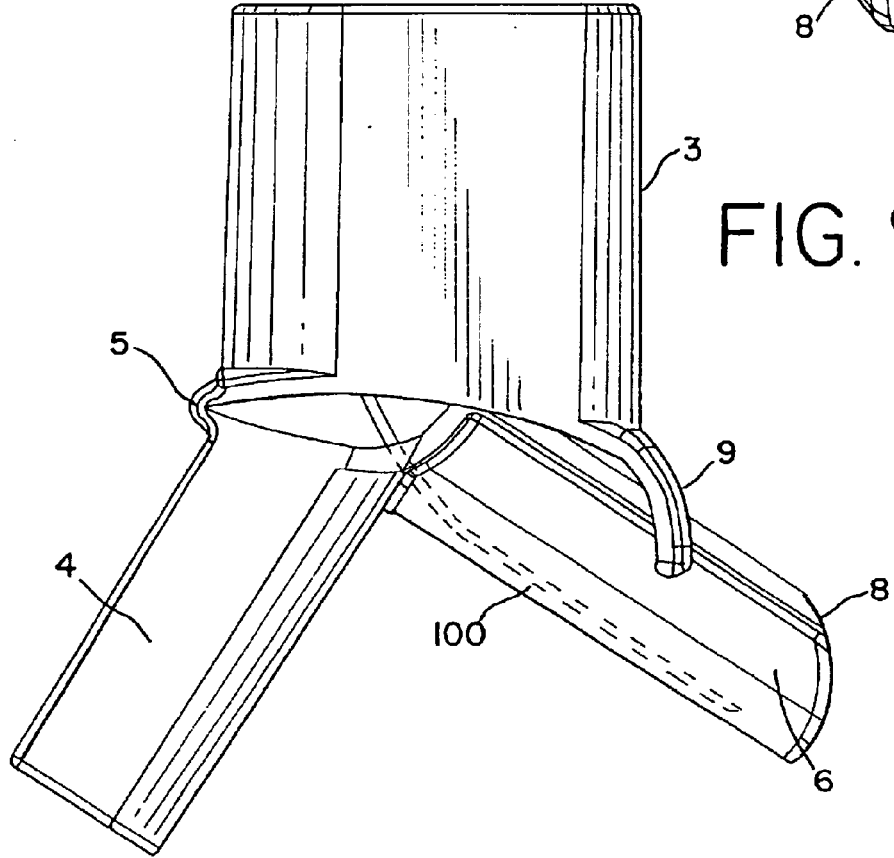
FIG. 9 is a side view showing the shield part pivoted to a locked position.

From FIG. 8 and FIG. 9 it appears that the barbs 11,12 are co-operating with the flanges 7,8 of the shield part in order to interlock the shield part in the pivoted position. The deformed material in the transition area 5 together with the bend needle provide a biasing effect between the flanges 7,8 and the barbs 11,12. The needle hereby closely abuts on the side of the half tube 6 ensuring that unintended contact with the needle is avoided. This becomes especially clear in FIG. 9 where a part of the hub is cut away.

Figure 10:
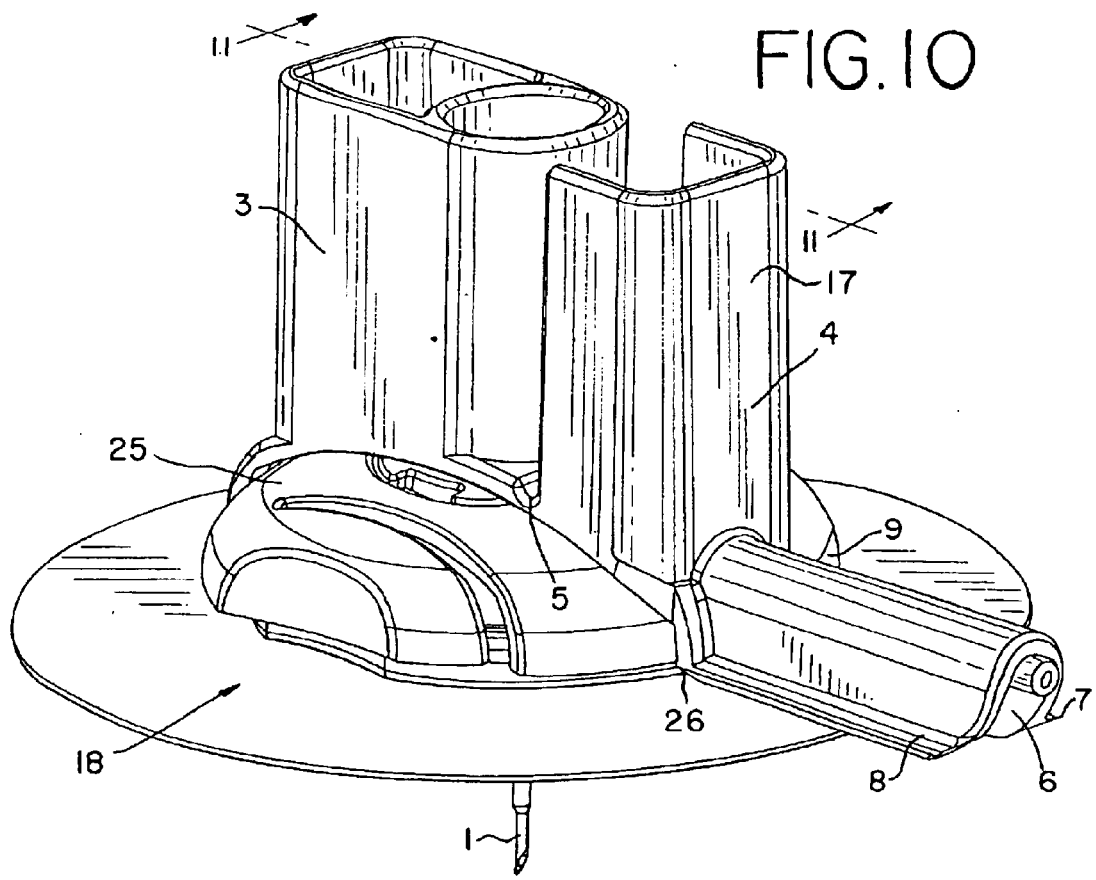
FIG. 10 is a perspective view where the medical puncturing device is mounted on an infusion device.
Figure 11:
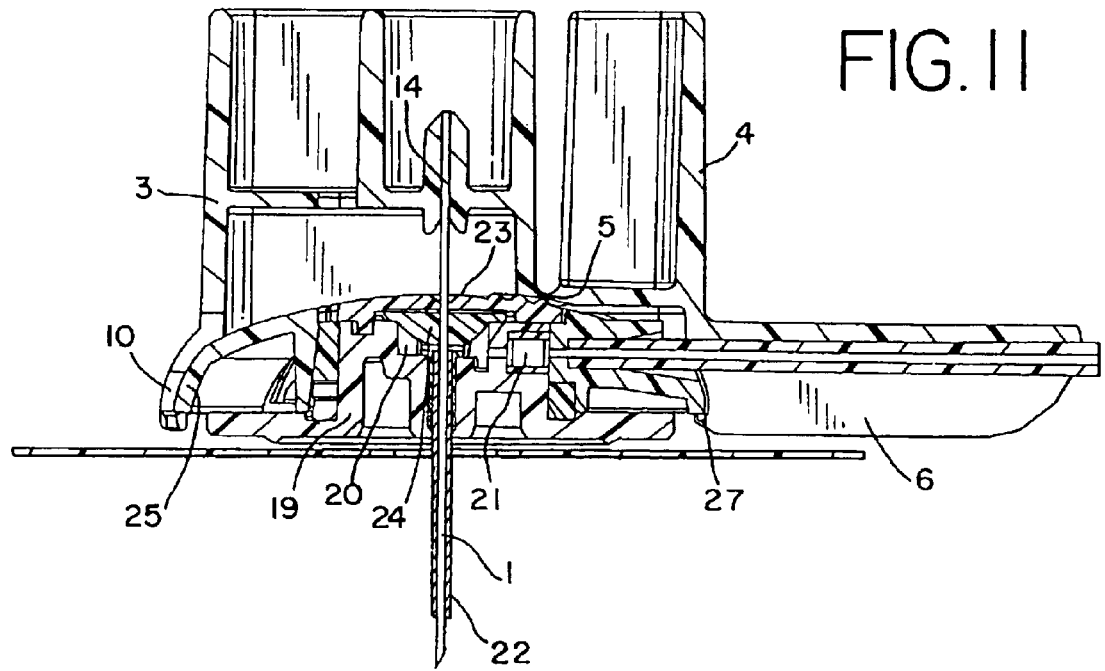
FIG. 11 is a sectional view after the line 11—11 in FIG. 10.

From FIG. 10 and FIG. 11 a field of use for the puncturing device appears. The puncturing device is inserted into an infusion device 18 for subcutaneous delivery of medication to a patient. This infusion device comprises a housing 19 in which a cavity 20 is provided and where a bore 21 leads medication from a pump or the like via a connector 25 to the cavity 20 where a soft cannula 22 is provided in fluid contact with the cavity 20 and where a further bore 23 covered with a self-sealing septum 24 is provided opposite the soft cannula 22. The puncturing device is inserted through the self-sealing septum 24, the cavity 20 and the soft cannula 22 and extends beyond the outer tip of the soft cannula. The puncturing device is held in place in relation to the connector 25 by means of barbs 26,27 on the shield part. When pressing the handle part 3 againts the pivoting handle 17 the barbs will release from their gripping position on the downward facing side of the connector 25 and the puncturing device may be retracted from the infusion set. The soft cannula is placed in an operational position, i.e. in a subcutaneous infusion site, by penetrating the skin and tissue of the patient by means of the puncturing device and afterwards retracting the puncturing device through the soft cannula, the cavity and the self-sealing septum. The puncturing device is not intended for further use and should therefore be folded and brought into a locked position as shown in FIG. 8 and FIG. 9 prior to discarding hereby ensuring that unintended harmful injuries caused by an exposed needle are avoided.

What is claimed is:

1. An infusion device comprising:
   a housing;
   a cavity within the housing;
   a soft cannula extending from the housing and being in flow communication with the cavity, said soft cannula having an outer tip;
   a medication bore within the housing for leading medication to said cavity;
   a puncturing device adapted to be connected to said housing, said puncturing device comprising a rigid needle being adapted to extend through the cannula and beyond the outer tip thereof when the puncturing device is connected to said housing, said rigid needle being at one end adapted for facilitating puncturing and including at the opposite end a hub;
   said hub having a hinge, a handle part and a single shield part with a first end and a second free end, said first end of the shield part being pivotably connected to the handle part by means of said hinge, whereby said second free end is pivotable with respect to said hinge;
   said shield part being adapted to cover the rigid needle when pivoted with respect to said hinge, the second free end of the shield part extending beyond said one end of the rigid needle; and
   said hub further having a locking mechanism on the shield part and the handle part, the locking mechanism being adapted to interlock the shield and the handle part in a pivoted position of the shield part when the puncturing device is disconnected from the housing and the shield part is pivoted to cover the rigid needle.

2. An infusion device as claimed in claim 1, wherein the locking mechanism on the handle part comprises two arms having on their opposed sides barbs adapted to interlock with the corresponding locking mechanism of the shield part.

3. An infusion device as claimed in claim 2, wherein the edges of the barbs are tapered so as to facilitate the insertion into the corresponding locking mechanism of the shield part.

4. An infusion device as claimed in claim 3, wherein the hub is formed as a single part and where the hinge between the handle part and the shield part is an area with a reduced rigidity.

5. An infusion device as claimed in claim 3, wherein the hub is made of a plastics material.

6. An infusion device as claimed in claim 3, wherein gripping means are provided on the shield part and the handle part, said gripping means being adapted to lock the hub to the housing.

7. An infusion device as claimed in claim 1, wherein the locking mechanism on the shield part comprises two side flanges adapted to interlock with the corresponding locking mechanism of the handle part.

8. An infusion device as claimed in claim 7, wherein the edges of the flanges are tapered so as to facilitate the insertion into the corresponding locking mechanism of the handle part.

9. An infusion device as claimed in claim 1, wherein the shield part comprises a recess for accommodating the rigid needle.

10. An infusion device as claimed in claim 1, wherein the shield part has an essentially U-shaped cross section.

11. An infusion device as claimed in claim 1, wherein the shield part comprises an operating handle, the operating handle thereby being pivotable with respect to the handle part of the hub.

12. An infusion device as claimed in claim 1, wherein the hub is formed as a single part and where the hinge between the handle part and the shield part is an area with a reduced rigidity.

13. An infusion device as claimed in claim 1, wherein the hub is made of a plastics material.

14. An infusion device as claimed in claim 1, wherein gripping means are provided on the shield part and the handle part, said gripping means being adapted to lock the hub to the housing.

15. An infusion device as claimed in claim 1, wherein gripping means are provided on the shield part and the handle part, said gripping means being adapted to lock the hub to the housing, wherein the shield part comprises an operating handle, the operating handle being pivotable with respect to the handle part of the hub, and wherein pressing the handle part against the operating handle will release the gripping means and thereby the puncturing device from the housing.

16. An infusion device comprising:
a housing;
a cavity within the housing;
a soft cannula extending from the housing and being in flow communication with the cavity, said soft cannula having an outer tip;
a medication bore within the housing for leading medication to said cavity;
a puncturing device adapted to be connected to said housing, said puncturing device comprising a rigid needle being adapted to extend through the cannula and beyond the outer tip thereof when the puncturing device is connected to said housing, said rigid needle being at one end adapted for facilitating puncturing and including at the opposite end a hub;
said hub having a hinge, a handle part and a single shield part with a first end and a second free end, said first end of the shield part being pivotably connected to the handle part by means of said hinge, whereby said second free end is pivotable with respect to said hinge;
said shield part being adapted to cover and bend the rigid needle when the shield part is pivoted with respect to said hinge, the second free end of the shield part extending beyond said one end of the rigid needle; and
said hub further having a locking mechanism on the shield part and the handle part, the locking mechanism being adapted to interlock the shield and the handle part in a pivoted position of the shield part when the puncturing device is disconnected from the housing and the shield part is pivoted to cover the rigid needle.

17. An infusion device as claimed in claim 16, wherein the locking mechanism on the handle part comprises two arms having on their opposed sides barbs adapted to interlock with the corresponding locking mechanism of the shield part.

18. An infusion device as claimed in claim 17, wherein the edges of the barbs are tapered so as to facilitate the insertion into the corresponding locking mechanism of the shield part.

19. An infusion device as claimed in claim 16, wherein the locking mechanism on the shield part comprises two side flanges adapted to interlock with the corresponding locking mechanism of the handle part.

20. An infusion device as claimed in claim 19, wherein the edges of the flanges are tapered so as to facilitate the insertion into the corresponding locking mechanism of the handle part.

21. An infusion device as claimed in claim in claim 16, wherein the shield part comprises a recess for accommodating the rigid needle.

22. An infusion device as claimed in claim 16, wherein the shield part has an essentially U-shaped cross section.

23. An infusion device comprising:
a housing;
a cavity within the housing;
a soft cannula extending from the housing and being in flow communication with the cavity, said soft cannula having an outer tip;
a bore for leading medication to said cavity;
a puncturing device adapted to be connected to said housing, said puncturing device comprising a needle being adapted to extend through the cannula and beyond the outer tip thereof when the puncturing device is connected to said housing, said needle being at one end adapted for facilitating puncturing and comprising an opposite end of a hub;
said hub comprising a handle part and a shield part, said shield part being pivotable in relation to the handle part;
said hub further comprising a locking mechanism on the shield part and the handle part, the locking mechanism being adapted to interlock the shield and the handle part in a pivoted position of the shield part when the puncturing device is disconnected form the housing, whereby the rigid needle is covered by the shield; and
wherein the needle is bendable when the shield part and the handle part are locked together, whereby the bendable needle provides a biasing effect between the locking mechanism on the shield part and the handle part, and whereby the bendable needle closely abuts on the shield to ensure that unintended contact with the needle is avoided.

* * * * *

UNITED STATES PATENT AND TRADEMARK OFFICE
CERTIFICATE OF CORRECTION

| | |
|---|---|
| PATENT NO. | : 6,840,922 B2 |
| APPLICATION NO. | : 10/017789 |
| DATED | : January 11, 2005 |
| INVENTOR(S) | : Jan W. Nielsen et al. |

It is certified that error appears in the above-identified patent and that said Letters Patent is hereby corrected as shown below:

<u>On the Title Page, Item (57) Abstract: Line 7,</u>

After "locking means being", delete "adapter" and substitute --adapted-- in its place.

Signed and Sealed this

Twentieth Day of November, 2007

JON W. DUDAS
*Director of the United States Patent and Trademark Office*